United States Patent [19]
Van Santen et al.

[11] Patent Number: 6,127,557
[45] Date of Patent: Oct. 3, 2000

[54] METHOD FOR PRODUCING SILASEQUIOXANE METAL COMPLEXES, NOVEL SILASESQUIOXANE METAL COMPLEXES AND USE THEREOF

[75] Inventors: Rutger Anthony Van Santen, Eindhoven; Hendrikus Cornesis Louis Abbenhuis, Breda; Martinus Lambertus Wilhelmus Vorstenbosch, Mariahout, all of Netherlands

[73] Assignee: Solvay Deutschland GmbH, Hannover, Germany

[21] Appl. No.: 09/403,260

[22] PCT Filed: Apr. 2, 1998

[86] PCT No.: PCT/EP98/01932

§ 371 Date: Oct. 18, 1999

§ 102(e) Date: Oct. 18, 1999

[87] PCT Pub. No.: WO98/46352

PCT Pub. Date: Oct. 22, 1998

[30] Foreign Application Priority Data

Apr. 16, 1997 [DE] Germany ............ 197 15 786
Oct. 5, 1997 [DE] Germany ............ 197 48 835

[51] Int. Cl.$^7$ ............ C07D 301/12; C07D 301/19; C07F 7/02; C07F 7/21; C07F 7/28
[52] U.S. Cl. ............ 549/529; 549/531; 556/10; 556/52; 556/460
[58] Field of Search ............ 549/529, 531; 556/10, 52, 460

[56] References Cited

FOREIGN PATENT DOCUMENTS

97/24344 7/1997 WIPO .

OTHER PUBLICATIONS

Buys et al, Journal of Molecular Catalysis, 86, pp. 309–315, 1994.
Feher et al, Polyhedron, 14(22), pp. 3239–3253, 1995.
Winkhofer et al, Angew. Chem. Ind. Eng., Engl. Commun., 33(13), pp. 1352–1354, 1994.

*Primary Examiner*—Ba K. Trinh
*Attorney, Agent, or Firm*—Evenson, McKeown, Edwards & Lenahan, P.L.L.C.

[57] ABSTRACT

A method for producing silasesquioxane metal complexes of the formula (II)

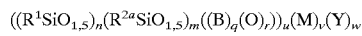

$$((R^1SiO_{1.5})_n(R^{2a}SiO_{1.5})_m((B)_q(O)_r))_u(M)_v(Y)_w$$

in which $R^1$ represents $C_5$–$C_{10}$-cycloalkyl, norbornyl or adamantyl; $R^{2a}$ represents oxygen; B represents H, OH, halogen, alkoxy, $SiR^3_y$, in which $R^3$ can be $C_1$–$C_4$ alkyl, aryl or substituted silyl groups, and y represents 2 or 3, and $R^1$ and $R^3$ can be functionalized; M represents metals of the 4$^{th}$ to 7$^{th}$ subgroups of the periodic system of elements; Y represents $C_1$–$C_{20}$ alkyl or aryl groups devoid of beta-hydrogen, silyl, alkoxy, OH, halogen, oxo, imido, fluorenyl, indenyl, cyclopentadienyl, in which the individual ligands can be substituted; n=6 or 7; m=0 or 1; q=0–2; r=0–2; u=1–4; v=1–4; w=0–12, in which a metal compound of the 4$^{th}$ to 7$^{th}$ subgroups of the periodic system of elements and at least one silasesquioxane compound of the formula (I)

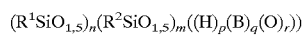

$$(R^1SiO_{1.5})_n(R^2SiO_{1.5})_m((H)_p(B)_q(O)_r))$$

in which $R^1$, B, n, m, q and r have the above meanings; $R^2$ represents OH, and p equals 0–4, are suspended in an alkylated aromatic hydrocarbon, optionally in the presence of a basic compound, with stirring at −80 to +110° C., and a reaction product is separated at room temperature. The invention also relates to metal complexes which include an oxidic metal cluster containing titanium atoms, in which each titanium atom has been coordinated ×6, and to the use of such metal complexes as catalysts for oxidation or epoxidation of unsaturated hydrocarbons or alcohols in an aqueous medium.

31 Claims, No Drawings

METHOD FOR PRODUCING SILASEQUIOXANE METAL COMPLEXES, NOVEL SILASESQUIOXANE METAL COMPLEXES AND USE THEREOF

This application is a 371 of PCT/EP98/01932 dated Apr. 2, 1998.

BACKGROUND OF THE INVENTION

The invention relates to a method for synthesizing silasesquioxane metal complexes, to new silasesquioxane metal complexes and to their use.

The synthesis of silasesquioxane metal complexes by the reaction of trisilanol, which is substituted by cyclohexyl groups, with a metal compound, is known (Polyhedron, 1995, vol. 14, No. 22, pages 3239–3253).

The synthesis of a trisilanol, containing cyclohexyl groups, is very time consuming. This trisilanol is, however, readily soluble, so that the reaction to the desired metal complexes is readily possible.

A trisilanol, which is substituted by cyclopentyl groups, can be synthesized in a much shorter time. However, the trisilanol is not very soluble, so that the synthesis of the corresponding metal complexes has not previously been described.

The previously known methods for the synthesis of the metal complexes are very time consuming and require large amounts of solvents, which must be worked up once again.

The use of titanium containing metal complexes as catalysts for the synthesis of epoxide compounds by the oxidation of unsaturated hydrocarbons is also known. For example, the WO 97/24344 discloses a method for the oxidation of olefinically unsaturated hydrocarbons, for which titanium silasesquioxane catalysts are used. However, this method is limited to organic hydroperoxides as oxidizing agents and can be carried out only in anhydrous organic solvents. The titanium atoms in the titanium silasesquixoane catalysts used are tetrahedrally coordinated four fold.

SUMMARY OF THE INVENTION

It is an object of the invention to provide a method for the synthesis of silasesquioxane metal complexes, with which the silasesquioxane metal complexes, which previously were accessible only with difficulty if at all, can be made available.

It is a further object of the invention to make the silasesquioxane metal complexes available as catalysts, which are also stable and catalytically active in aqueous media, for the oxidation of unsaturated hydrocarbons or alcohols, since in this way environmentally-friendly oxidizing agents, such as oxygen or hydrogen peroxide, can be used, for example, for the epoxidation of alkene compounds.

The object of the invention is achieved due to the fact that the reaction of the metal compounds with a silasesquioxane with a defined denticulation takes place in a suspension.

Pursuant to the invention, halides, especially chlorides, $C_1$ to $C_{20}$ alkyl or aryl compounds, which do not contain a beta hydrogen atom, such as methyl, benzyl, neopentyl, xylyl, mesityl, neophil and/or adamantyl compounds, silyl, fluorenyl, indenyl and/or cyclopentadienyl compounds, it being possible for the individual ligands to be substituted by $C_1$ to $C_4$ alkyl, $C_1$ to $C_4$ alkylsilyl, alkoxy, aryl or arylsilyl groups, oxides, imides, amides, alkoxides (such as —OR, in which R is hydrogen, $C_1$ to $C_{20}$ alkyl, especially methyl, ethyl, isopropyl, t-butyl, aryl, especially benzyl, phenyl, toluyl, naphthyl, xylyl) or mixed compounds of these, such as oxohalides, aryl or alkyl halides, halogen amides or alkylalkoxides of the metals of the $4^{th}$ to the $7^{th}$ subgroups of the Periodic Table of the Elements and at least one silasesquioxane of the general formula I

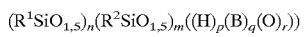

in which $R^1$ is $C_5$ to $C_{10}$ cycloalkyl, especially cyclopentyl, cyclohexyl, cycloheptyl, norbornyl, adamantyl $R^2$ is OH B is H, OH halogen, alkoxy or $SiR^3_y$, wherein $R^3$ is $C_1$ to $C_4$ alkyl, especially methyl, aryl, particularly phenyl or $SiMe_2(CH_2)_sCH=CH_2$, $SiMe_2(CH_2)_sCH_2CH_2A$, $SiMe_2(CH_2)_sCHACH_3$, wherein A represents OH, COOH, $NH_2$, $SO_3$—, COO— and s represents 1 to 20, y represents 2 and 3, and $R^1$ and $R^3$ can be functionalized by halogen or OH, and n is 6 and 7 m is 0 and 1 p is 0 to 4 q is 0 to 2 r is 0 to 2 are suspended in an organic solvent, such as an alkylated aromatic hydrocarbon, optionally in the presence of a basic compound, with stirring at −80° C. to +110° C. and the reaction product is removed at room temperature.

Metals, within the sense of the invention, are understood to include, in particular, titanium, zirconium, hafnium, chromium, tungsten, molybdenum, vanadium, niobium, tantalum and rhenium; titanium, vanadium or zirconium being preferred.

As metal compounds, $TiCl_4$, $TiCpCl_3$, $TiCl_3(\eta^5-C_5H_3(SiMe_3)_2-1.3)$, zirconyl alkyl compounds, zirconyl alkyl aryl compounds, $VO(Oi-alkyl)_3$, especially $VO(Oi-propyl)_3$ and/or $VOCl_3$ are used.

As basic compound, preferably an organic base is used.

The by-products are removed simply by centrifuging.

The silasesquioxane metal complexes can be precipitated directly from the supernatant solution, for example, by the addition of protic solvents, which are miscible with water, such as i-propanol, ethanol, acetone and/or acetonitrile and purified by known methods, such as recrystallization.

The inventive method for the synthesis of silasesquioxane metal complexes of the general formula II

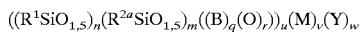

in which $R^1$, B, n, m q, r have the meanings given above $R^{2a}$ is oxygen, u is 1 to 4 v is 1 to 4 w is 0 to 12

M represents the metals and Y the above-named groups of the metal compounds, which are linked to the metal, is distinguished from previously known methods owing to the fact that the solvent requirement can be reduced drastically. The time-consuming working up steps can thus be omitted.

DETAILED DESCRIPTION OF PREFERRED EMBODIMENTS

In one embodiment of the inventive method, preferably compounds of titanium and zirconium, especially $TiCl_4$, TiCl$_3$($\eta^5$-C$_5$H$_5$) or TiCl$_3$($\eta^5$-C$_5$H$_3$) (SiMe$_3$)$_2$1,3) or Zr(CH$_2$C$_6$H$_5$)$_4$, are used as metal compounds.

In a different embodiment, preferably silasesquioxanes of the general formula I are used, in which a) n=7, m=1, q=p=r=0
   R$^1$=c-C$_5$H$_9$, c-C$_6$H$_{11}$, c-C$_7$H$_{13}$
   R$^2$=OH b) n=7, m=0, p=q=1, r=1.5
   R$^1$=c-C$_5$H$_9$, c-C$_6$H$_{11}$, c-C$_7$H$_{13}$
   B=SiR$^3_2$ (wherein R$^3$ represents the above-mentioned substituents, especially methyl or phenyl)

c) n=7, m=0, p=1, q=2, r=1.5
   R$^1$=c-C$_5$H$_9$, c-C$_6$H$_{11}$, c-C$_7$H$_{13}$
   B=SiR$^3_3$ (wherein R$^3$ represents the above-mentioned substituents, especially methyl or phenyl)

d) n=7, m=0, p=2, q=1, r=1.5
   R$^1$=c-C$_5$H$_9$, c-C$_6$H$_{11}$, c-C$_7$H$_{13}$
   B=SiR$^3_3$ (wherein R$^3$ represents the above-mentioned substituents, especially methyl or phenyl)

e) n=7, m=q=0, p=3, r=1.5
   R$^1$=c-C$_5$H$_9$, c-C$_6$H$_{11}$, c-C$_7$H$_{13}$ f) n=6, m=q=0, p=4, r=2
   R$^1$=c-C$_7$H$_{13}$, norbornyl.

In a further embodiment, silasesquioxanes of the general formula I are used, in which R$^1$ represents c-C$_5$H$_9$.

In a different embodiment, titanium silasesquioxane complexes are synthesized, in that a titanium compound is suspended with a silasesquioxane (I) in an alkylated aromatic hydrocarbon, preferably in toluene, at a temperature of 20° C. to 50° C. With the addition of a basic compound, preferably pyridine, the suspension is stirred further, the temperature being maintained at about 50° C. The mixture is cooled to room temperature and the by-products are removed, preferably by centrifuging.

It was found that new 4-fold or 6-fold coordinated metal complexes can be synthesized, which represent catalysts suitable for the oxidation of unsaturated hydrocarbons and alcohols in an aqueous medium.

The inventive, new metal complexes comprise, in particular, metal complexes containing titanium atoms, in which each titanium atom is coordinated 6 fold. This structural distinguishing characteristic of the 6-fold coordination of all titanium atoms represents an important prerequisite for the hydrolysis resistance of the inventive metal complexes and for their catalytic effectiveness in an aqueous medium. Usually, a metal cluster, contained in inventive metal complexes, has 4 tetrahedrally disposed titanium atoms, each titanium atom being surrounded octahedrally in a first coordination sphere by 6 oxygen atoms. Aside from being bonded to the titanium atom, these Oxygen atoms can form further bonds, preferably with hydrogen, carbon or silicon atoms. It was found that at least two of the titanium atoms in the oxidic metal cluster are bridged to one another over a hydroxyl group. As a rule, the metal cluster, contained in the metal complexes, is formed jointly by four titanium atoms and four hydroxyl groups, three titanium atoms being bridged in each case with one another over a hydroxyl group. In this way, the titanium atoms form a cuboid (=distorted cube) with the bridging hydroxyl groups. In the cuboid, in each case three of the four titanium atoms have the identical coordinative surroundings and in each case three of the four hydroxyl groups have the same surroundings. In this way, three of the six coordination sites of the titanium atoms are occupied in each case by one bond to a bridging hydroxyl group. In a preferred embodiment, the three remaining coordination sites of the titanium atom are occupied by oxygen atoms, which originate from at least 4-denticulate ligands. It is advantageous if the three coordination sites of the aforementioned titanium atoms, which do not form bonds with the bridging hydroxyl groups, are occupied by oxygen atoms originating from silasesquioxane ligands. For example, these coordination sites of the titanium atoms, which do not bridge hydroxyl groups, can be occupied by a total of three 4-denticulate silasesquioxane ligands of the general formula (R$_6$(Si$_6$O$_7$)O$_4$), in which R represents C$_5$ to C$_{10}$ cycloalkyl, adamantyl or norbornyl.

The metal complexes of the general formula III

III

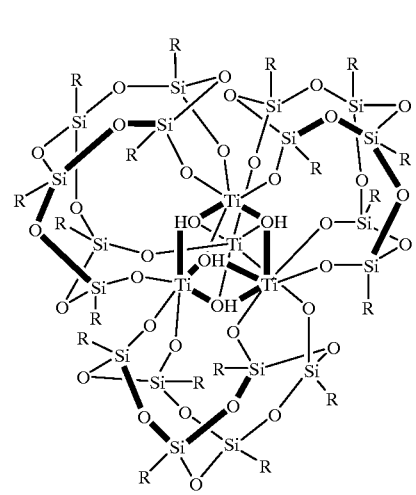

in which R has the meaning given above for R$^1$, are particularly preferred inventive metal complexes.

In these compounds of formula III, R preferably represents cycloheptyl or norbornyl.

Compounds of formula III can be synthesized by reacting compounds of the general formula IV

IV

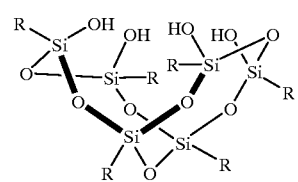

in which R has the meaning given above for R$^1$, with titanium tetrachloride.

Tetrasilanols of formula IV are partly known from Feher et al., Organometallics 10 (1991), pages 2526 to 2528 as well as from Feher et al., Polyhedron 14 (1995), pages 3239 to 3253, and can be synthesized according to the methods described there or according to similar methods.

In a further embodiment, the reaction of the tetrasilanols of formula IV with titanium tetrachloride takes place at temperatures of −60° C. to 110° C. Preferably, the reactants are mixed at room temperature and the temperature subsequently is raised to 30° C. to 80° C. and preferably to 40° C. to 60° C. for 1 to 10 minutes to complete the reaction and, before the product is worked up, the temperature is lowered to room temperature. Organic solvents, such as methylene chloride or optionally monosubstituted or multisubstituted benzenes, substituted at the benzene ring by a low molecular weight alkyl, such as toluene, are used as solvents. Advantageously, a small amount of an organic base, such as a tertiary low molecular weight alkylamine, such as triethylamine or pyridine, can be added to the reaction mixture before the temperature is raised.

The metal complexes of formula III are obtained from the synthesis as racemates. Therefore, the racemic mixtures as well as the pure enantiomers of metal complexes of formula III are an object of the invention.

In a different, preferred embodiment, a zirconium compound is suspended with a silasesquioxane in toluene at −80° C. The mixture is heated with stirring to room temperature and the by-products are removed by known procedures.

It was found that it is possible to synthesize these zirconium silasesquioxane complexes without having to add a basic compound, such as pyridine.

The inventive method enables, for example, silasesquioxane metal complexes of the general formula II to be synthesized, in which 1) $n=7$, $m=1$, $q=r=0$, $u=4$, $v=1$, $w=0$
   $R^1=$c-$C_5H_9$, c-$C_6H_{11}$, c-$C_7H_{13}$, norbornyl
   $R^{2a}=$oxygen
   M=Ti, Zr, Hf 2) $n=7$, $m=0$, $q=1$, $r=15$, $u=4$
   $v=1$, $w=0$
   $R^1=$c-$C_5H_9$, c-$C_6H_{11}$, c-$C_7H_{13}$, norbornyl
   $B=SiR^3_2$ (in which $R^3$ has the meaning given above)
   M=Ti, Zr, Hf 3) $n=7$, $m=0$, $q=2$, $r=1.5$, $u=4$
   $v=1$, $w=0$
   $R^1=$c-$C_5H_9$, c-$C_6H_{11}$, c-$C_7H_{13}$, norbornyl
   $B=SiR^3_3$ (in which $R^3$ has the meaning given above)
   M=Ti, Zr, Hf 4) $n=7$, $m=0$, $q=1$, $r=1.5$
   $u=2$, $v=1$, $w=0$
   $R^1=$c-$C_5H_9$, c-$C_6H_{11}$, c-$C_7H_{13}$, norbornyl
   $B=SiR^3_3$ (in which $R^3$ has the meaning given above)
   M=Ti, Zr, Hf 5) $n=7$, $m=0$, $q=1$, $r=1.5$
   $u=2$, $v=1$, $w=1$
   $R^1=$c-$C_5H_9$, c-$C_6H_{11}$, c-$C_7H_{13}$, norbornyl
   $B=SiR^3_3$ (in which $R^3$ has the meaning given above)
   M=Cr, Mo, W
   Y=oxo, imido 6) $n=7$, $m=q=0$, $r=1.5$
   $u=1$, $v=1$, $w=1$
   $R^1=$c-$C_5H_9$, c-$C_6H_{11}$, c-$C_7H_{13}$, norbornyl
   M=Ti, Zr, Hf
   Y=has the meaning given above and preferably represents cyclopentadienyl, methyl, benzyl, neopentyl, OH, halogen, alkoxide.

7) $n=7$, $m=q=0$, $r=1.5$, $u=1$
   $v=1$, $w=1$
   $R^1=$c-$C_5H_9$, c-$C_6H_{11}$, c-$C_7H_{13}$, norbornyl
   M=V, Nb, Ta
   Y=oxo, imido 8) $n=6$, m $q=0$, $r=2$, $u=1$, $v=1$, $w=0$
   $R^1=$c-$C_7H_{13}$, norbornyl
   M=Ti, Zr, Hf 9) $n=6$, $m=q=0$, $r=2$
   $u=v=w=1$
   $R^1=$c-$C_7H_{13}$, norbornyl
   M=Cr, Mo, W
   Y=oxo, imido 10) $n=6$, $m=q=0$, $r=2$, $u=1$, $v=2$
    $w=4$
    $R^1=$c-$C_7H_{13}$, norbornyl
    M=Cr, Mo, W
    Y=oxo, imido 11) $n=6$, $m=q=0$, $r=2$, $u=1$
    $v=4$, $w=12$
    $R^1=$c-$C_7H_{13}$, norbornyl
    M=Re
    Y=oxo, imido.

The inventive method enables silasesquioxane metal complexes to be synthesized using silasesquioxanes containing cyclopentyl groups. It was found that these metal complexes can be synthesized in a very short time. The reaction time is only a few minutes.

Such metal complexes could not be synthesized previously because of the poor solubility of the silasesquioxane containing the cyclopentyl groups.

The inventive method furthermore enables uni-dentate and multi-dentate silasesquioxane metal complexes to be synthesized. It is also possible to synthesize metal complexes coordinated 4-fold and 6-fold. The synthesis of silasesquioxane polymetal complexes is also possible.

The metal complexes, synthesized pursuant to the invention, are stable, microcrystalline solids.

It was furthermore found that the metal complexes, synthesized pursuant to the invention, are catalytically active and suitable, particularly, as catalysts for the oxidation or epoxidation of unsaturated hydrocarbons, including halogenated alkenes and alcohols.

Because the active centers in the metal complex are defined precisely and, accordingly, the leaching behavior can be checked and controlled, the inventive use of the silasesquioxane metal complexes as catalyst is particularly advantageous in comparison to the use of the previously known catalysts.

In particular, the metal complexes of formula III, which are obtained, can be used for the oxidation or epoxidation of unsaturated hydrocarbons or alcohols. For this purpose, compounds of formula III, if so desired, can be applied in a known manner on conventional, oxidic catalyst supports, such as silica, and preferably on catalyst supports with an average pore width of between 30 and 200 Å. Organic or inorganic oxidizing agents can be used in the oxidation reactions, catalyzed by the inventive metal complexes. Suitable organic oxidizing agents are, for example, organic hydroperoxides, such as t-butyl hydroperoxide (=TBHP) or ethylbenzene hydroperoxide. Suitable inorganic oxidizing agents are, for example, hydrogen peroxide. The oxidization reactions can be carried out in suitable organic solvents, such as alcohols, hexane, toluene or in an aqueous medium.

If the oxidation reactions are carried out in an aqueous medium, the use of multi-dentate silasesquioxane metal complexes is required. It was found that the multi-dentate metal complexes hydrolyze only partially, if at all, in aqueous systems. With that, they retain a defined structure and, accordingly, their catalytic activity.

The following examples are intended to explain the invention without limiting it.

TEST OF THE CATALYTIC EFFECTIVENESS

The test of the catalytic effectiveness of the inventive metal complexes was carried out in a 1.5 ml batch reactor with a stirrer at a controlled temperature. For each experiment, 4.5 mg of $((c-C_7H_{13})_6Si_6O_{11})_3(TiOH)_4$ was dissolved in 750 liters of toluene as oxidation catalyst. Subsequently, 750 liters of the appropriate alkene were added. The resulting mixture was heated in each case to 80° C., before a solution of the oxidizing agent in a suitable organic or inorganic solvent was added. The amount of the epoxidized product, obtained in the individual experiments by oxidizing the unsaturated starting compound, was determined in each case by means of $^1$H-NMR spectroscopy and stated in the following Table as a percentage of epoxide relative to the starting amount of peroxide.

TABLE

| Example No. | Alkene | Oxidizing Agent | T (° C.) | Alkene/ Oxidizing Agent | Oxidizing Agent/ Catalyst | Conversion of the Oxidizing Agent (%) | Selectivity to the Epoxide (%) |
|---|---|---|---|---|---|---|---|
| 1 | cyclooctene | TBHP | 80 | 23 | 178 | 100 | 60 (0.5 h) |
| 2 | 1-octene | TBHP | 80 | 19 | 178 | 100 | 20 (1 h) |
|   |   |   |   |   |   |   | 60 (18 h) |
| 3 | cyclooctene | H$_2$O$_2$ | 80 | 48, 24, 16, 12 | 85, 171, 257, 343 | 100 | >90 (1 h) |
| 4 | 1-octene | H$_2$O$_2$ | 80 | 40 | 85 | 100 | 10 (3 h) |

In experiments 1 and 2, a solution of TBHP in toluene was used as oxidizing agent. The total amount of TBHP in each case was 22.5 mg. In experiments 3 and 4, an aqueous solution of hydrogen peroxide was used as oxidizing agent. In this case, only half the amount of oxidizing agent was used (10 liters of a 35% aqueous hydrogen peroxide solution) and the reaction mixture was checked after 1 hour for completion of the reaction. In experiment 3, the reaction was started subsequently once again by the addition of further hydrogen peroxide and, at the end of a further hour, the reaction mixture was checked once more for its content of epoxidized product. It was possible to repeat this procedure 3 times without observing a decrease in the catalytic activity of the titanium complex. This confirms that the catalytic compound is resistant to hydrolysis and to hydrogen peroxide.

EXAMPLE 1

Under an atmosphere of nitrogen and with stirring, 0.178 mL of TiCl$_4$ were added at room temperature to a solution of 1.13 g of (c-C$_7$H$_{13}$)$_6$Si$_6$O$_7$(OH)$_4$ in 30 mL of toluene. To the resulting reaction mixture, 0.65 mL of pyridine were added, whereupon a yellowish suspension was formed. This suspension was heated for 2 minutes at 50° C. Subsequently, it was allowed to cool to room temperature, 0.5 ml of water were added and the mixture was stirred for some time and filtered to remove the pyridinium chloride that was formed and the filtrate was concentrated under vacuum. The white solid obtained was crystallized in air from a mixture of 20 mL of toluene and 50 mL of acetonitrile. A microcrystalline (c-C$_7$H$_{13}$)$_6$Si$_6$O$_{11}$)$_3$(TiOH)$_4$, $^1$H-NMR(300 MHz, CDCl$_3$, 23C, SiMe$_4$): δ=1.90–1.75 (m, 4H), 1.59–1.35 (m, 8H), 0.91–0.87 (m, 1H), was obtained in an amount of 0.80 g, which corresponds to a yield of 86%.

EXAMPLE 2

Synthesis of (Ti(η$^5$-C$_5$H$_3$(SiMe$_3$)$_2$-1,3) ((c-C$_5$H$_9$)$_7$Si$_7$O$_{12}$))

To a suspension of 1.38 g of (TiCl$_3$(η$^5$-C$_5$H$_3$(SiMe$_3$)$_2$-1, 3), 3.40 g of (c-C$_5$H$_9$)$_7$Si$_7$O$_9$(OH)$_3$ and 50 ml of toluene, 1.5 ml of pyridine is added at 30° C. with stirring within a period of 15 seconds. The yellowish suspension formed is heated to 50° C. and, after 2 minutes, cooled to room temperature. The reaction products and the unreacted starting materials are removed by centrifuging. The supernatant clear yellow solution is mixed with ethanol (300 mL). The metal complex is precipitated as a microcrystalline powder. Yield: 79%

EXAMPLE 3

Synthesis of ((c-C$_5$H$_9$)$_7$Si$_7$O$_{11}$(OSiMe$_3$))$_2$Ti

To a suspension of 1.03 g of (c-C$_5$H$_9$)$_7$Si$_7$O$_9$(OSiMe$_3$) (OH)$_2$ and 0.09 mL of TiCl$_4$ in 30 ml of toluene, 0.22 ml of pyridine are added with stirring at 20° C. within a period of 1 minute. The suspension is heated to 50° C. and, after 2 minutes, cooled to room temperature. The mixture is centrifuged. The clear yellow supernatant solution is removed and mixed with 200 ml of ethanol. The metal complex is precipitated as a white, microcrystalline powder. Yield: 87%

EXAMPLE 4

Synthesis of (c-C$_5$H$_9$)$_7$Si$_7$O$_{12}$V=O

To a suspension of 1.01 g of (c-C$_5$H$_9$)$_7$Si$_7$O$_9$(OH)$_3$ in 20 ml of toluene, 0.29 g of (i-PrO)$_3$V=O, dissolved in 2 ml of toluene, are added within a period of 15 seconds. This mixture is heated within 1 minute at 50° C. and cooled within 30 minutes to room temperature. After that, the mixture is centrifuged and the supernatant solution is removed. The solution is mixed with 80 ml of acetonitrile. The metal complex is precipitated as a white powder. Yield: 59%

What is claimed is:

1. A method for synthesizing silasesquioxane metal complexes, said method comprising suspending:

(a) a metal compound selected from the group consisting of halides, C$_1$ to C$_{20}$ alkyl or aryl compounds which do not contain a beta hydrogen atom, silyl, fluorenyl, indenyl and/or cyclopentadienyl compounds, in which individual ligands optionally may be substituted by C$_1$ to C$_4$ alkyl, C$_1$ to C$_4$ alkylsilyl, alkoxy, aryl or arylsilyl groups, oxides, imides, amides, alkoxides, and mixed compounds thereof of a metal from the 4$^{th}$ to the 7$^{th}$ subgroups of the Periodic Table of the Elements; and (b) at least one silasesquioxane of formula I:

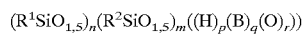

$(R^1SiO_{1.5})_n(R^2SiO_{1.5})_m((H)_p(B)_q(O)_r))$ wherein

R$^1$ is C$_5$ to C$_{10}$ cycloalkyl;

R$^2$ is OH;

B is H, OH, halogen, alkoxy or SiR$^3{}_y$, wherein R$^3$ is C$_1$ to C$_4$ alkyl, aryl, or SiMe$_2$(CH$_2$)$_s$CH=CH$_2$, SiMe$_2$(CH$_2$)$_s$CH$_2$CH$_2$A, SiMe$_2$(CH$_2$)$_s$CHACH$_3$, wherein A represents OH, COOH, NH$_2$, SO$_3$—, COO—, and s represents 1 to 20, y represents 2 or 3, and R$^1$ and R$^3$ can be functionalized by halogen or OH, and n is 6;

m is 0 or 1;

p is 0 to 4;

q is 0 to 2; and r is 0 to 2;

in an organic solvent with stirring at −80° C. to +110° C., and removing the resulting reaction product at room temperature.

2. A method according to claim 1, wherein the reaction is carried out in the presence of a basic compound.

3. A method according to claim 1, wherein said organic solvent is an alkylated aromatic hydrocarbon.

4. A method according to claim 1, wherein $R^3$ is methyl or phenyl.

5. A method according to claim 1, wherein $R^1$ is cyclopentyl, cyclohexyl, cycloheptyl, norbornyl or adamantyl.

6. A method according to claim 1, wherein said metal compound is an alkoxide —OR, wherein R is hydrogen, $C_1$ to $C_{20}$ alkyl, or aryl group.

7. A method according to claim 6, wherein R represents a methyl, ethyl, isopropyl, t-butyl, benzyl, phenyl, toluyl, naphthyl, or xylyl group.

8. A method according to claim 1, wherein said metal compound is a methyl, benzyl, neopentyl, xylyl, mesityl, neophil or adamantyl compound.

9. A method according to claim 1, wherein said metal compound is a mixed compound selected from the group consisting of oxohalides, aryl halides, alkyl halides, halogen amides, and alkylalkoxides of a metal from the $4^{th}$ to the $7^{th}$ subgroups of the Periodic Table of the Elements.

10. A method according to claim 1, wherein said metal compound is $TiCpCl_3$ or $Ti(\eta^5-C_5H_3)(SiMe_3-1,3)Cl_3$, and said metal compound and at least one silasesquioxane of formula I are suspended in toluene at 20° C. to 50° C. in the presence of pyridine as a basic compound.

11. A method according to claim 1, wherein said metal compound is a zirconium alkyl or zirconium alkylaryl compound, and said metal compound and at least one silasesquioxane of formula I are suspended in toluene at −80° C. to −20° C. and thereafter heated with stirring to room temperature.

12. A method according to claim 1, wherein said metal compound is $TiCl_4$, and said metal compound and at least one silasesquioxane of formula I are suspended in toluene at 20° C. to 50° C. in the presence of pyridine as a basic compound.

13. A method according to claim 1, wherein said metal compound is a $VO(Oialk)_3$ compound or $VOCl_3$, and said metal compound and at least one silasesquioxane of formula I are suspended in toluene.

14. A method according to claim 13, wherein said metal compound is $VO(Oiprop)_3$.

15. A silasesquioxane metal complex corresponding to the formula II:

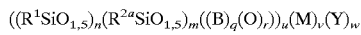

wherein $R^1$ is $C_5$ to $C_{10}$ cycloalkyl;

$R^{2a}$ is oxygen,

B is H, OH, halogen, alkoxy or $SiR^3_y$, wherein $R^3$ is $C_1$ to $C_4$ alkyl, aryl, or $SiMe_2(CH_2)_sCH=CH_2$, $SiMe_2(CH_2)_sCH_2CH_2A$, $SiMe_2(CH_2)_sCHACH_3$, wherein A represents OH, COOH, $NH_2$, $SO_3$—, COO—, and s represents 1 to 20, n is 6;

m is 0 or 1;

q is 0 to 2;

r is 0 to 2;

u is 1 to 4 v is 1 to 4, and w is 0 to 12.

16. A metal complex according to claim 15, comprising an oxidic metal cluster in which each metal atom is coordinated 4-fold or 6-fold, wherein said complex is stable in aqueous solution.

17. A metal complex according to claim 16, wherein the oxidic metal cluster contains 4 titanium atoms in a tetrahedral arrangement, each titanium atom being surrounded in a first coordination sphere octahedrally by 6 oxygen atoms.

18. A metal complex according to claim 17, wherein hydrogen, carbon or silicon is additionally linked to the oxygen atoms octahedrally surrounding each titanium atom.

19. A metal complex according to claim 18, wherein at least two titanium atoms in the oxidic metal cluster are bridged to one another via a hydroxyl group.

20. A metal complex according to claim 19, wherein 3 of the 4 titanium atoms each have the same coordinative surroundings and 3 of the 4 hydroxyl groups each have the same coordinative surroundings.

21. A metal complex according to claim 19, wherein the remaining three free coordination sites of the 6-fold coordinated titanium atoms are each occupied by one oxygen atom belonging to the silasesquioxane ligand.

22. A metal complex according to claim 21, comprising 3 silasesquioxane ligands of the formula $(R_6(Si_6O_7)O_4)$, wherein R represents $C_5$ to $C_{10}$ cycloalkyl, adamantyl or norbornyl.

23. A metal complex according to claim 22, corresponding to formula III:

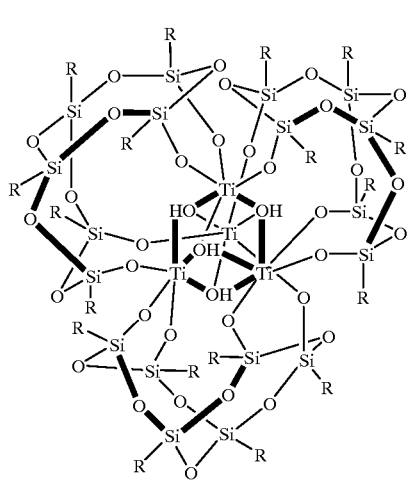

wherein R represents $R^1$.

24. A metal complex according to claim 23, R represents cycloheptyl or norbornyl.

25. A supported catalyst comprising a metal complex according to claim 15, supported on an oxidic support material having an average pore width of 30 to 200 Å.

26. A method of oxidizing an unsaturated hydrocarbon or an alcohol, said method comprising oxidizing said unsaturated hydrocarbon or alcohol in the presence of a catalytically effective amount of a complex according to claim 15, whereby an oxidized or epoxidized product is obtained.

27. A method according to claim 26, wherein the oxidization is carried out in an aqueous medium.

28. A method according to claim 27, wherein hydrogen peroxide is used as an oxidizing agent.

29. A method of synthesizing an epoxide compound, said method comprising reacting an unsaturated hydrocarbon or alcohol with an organic or inorganic hydroperoxide in the presence of a metal complex according to claim 15.

30. A method according to claim 29, wherein the reaction is carried out in an aqueous medium.

31. A method according to claim 30, wherein hydrogen peroxide is used as an oxidizing agent.

* * * * *